(12) United States Patent
Fiore

(10) Patent No.: US 9,498,441 B2
(45) Date of Patent: Nov. 22, 2016

(54) NITAZOXADINE COMPOSITION AND PROCESS TO PREPARE SAME

(75) Inventor: Esteban Alejandro Fiore, Ciudad de Buenos Aires (AR)

(73) Assignee: SIEGFRIED RHEIN S.A. DE C.V., Delg. Alvaro Obregon (MX)

( * ) Notice: Subject to any disclaimer, the term of this patent is extended or adjusted under 35 U.S.C. 154(b) by 0 days.

(21) Appl. No.: 14/374,862

(22) PCT Filed: Jan. 27, 2012

(86) PCT No.: PCT/IB2012/050380
§ 371 (c)(1),
(2), (4) Date: Oct. 6, 2014

(87) PCT Pub. No.: WO2013/110975
PCT Pub. Date: Aug. 1, 2013

(65) Prior Publication Data
US 2015/0064262 A1 Mar. 5, 2015

(51) Int. Cl.
A61K 9/16 (2006.01)
A61K 31/426 (2006.01)
A61K 9/00 (2006.01)
A61K 9/50 (2006.01)

(52) U.S. Cl.
CPC ............. *A61K 9/1652* (2013.01); *A61K 9/009* (2013.01); *A61K 9/0095* (2013.01); *A61K 9/1635* (2013.01); *A61K 9/1676* (2013.01); *A61K 9/5026* (2013.01); *A61K 9/5078* (2013.01); *A61K 9/5084* (2013.01); *A61K 31/426* (2013.01)

(58) Field of Classification Search
CPC ...................................................... A61K 9/16
USPC ................................................ 424/489, 490
See application file for complete search history.

(56) References Cited

U.S. PATENT DOCUMENTS

| | | | |
|---|---|---|---|
| 3,657,267 A | 4/1972 | Van Gelder et al. | |
| 3,950,351 A | 4/1976 | Rossignol et al. | |
| 4,017,647 A * | 4/1977 | Ohno .................. | A61K 9/2866 424/463 |
| 5,387,598 A | 2/1995 | Rossignol | |
| 5,968,961 A * | 10/1999 | Rossignol ............ | A61K 31/426 514/371 |
| 6,117,894 A | 9/2000 | Rossignol | |
| 8,007,527 B2 | 8/2011 | Han et al. | |
| 2004/0253323 A1* | 12/2004 | Giles .................... | A61K 31/352 424/702 |
| 2005/0171169 A1 | 8/2005 | Rossignol | |
| 2006/0057197 A1* | 3/2006 | Han ..................... | A61K 9/1652 424/468 |
| 2007/0116729 A1 | 5/2007 | Palepu | |
| 2007/0167504 A1 | 7/2007 | Rossignol | |
| 2007/0270375 A1* | 11/2007 | Quinn .................. | C07H 15/256 514/53 |
| 2008/0299188 A1 | 12/2008 | Appel et al. | |
| 2009/0182042 A1* | 7/2009 | Reddell ................. | A01N 43/20 514/475 |
| 2010/0209505 A1 | 8/2010 | Rossignol et al. | |
| 2011/0244050 A1 | 10/2011 | Fiore | |

FOREIGN PATENT DOCUMENTS

| | | |
|---|---|---|
| WO | WO 98/50035 | 11/1998 |
| WO | WO 2010/067140 A1 | 6/2010 |
| WO | WO 2010/093854 A1 | 8/2010 |

OTHER PUBLICATIONS

Allen, Loyd V., et al., "Ansel's Pharmaceutical Dosage Forms and Drug Delivery Systems" $8^{th}$ Edition, 2005, pp. 251, 252, 260-264, Lippincot Williams & Wilkins, Philadelphia.
International Search Report mailed Aug. 30, 2012 in International Application No. PCT/IB2012/050380, filed Jan. 27, 2012.
Davila-Gutierrez C.E. et al, "Nitazoxanide compared with Quinfamide and Mebendazole in the treatment of Helmiinthic infections and intestinal protozoa in children"; Am J Trop Med Hyg. 2002, 66(3): 251-254.
Milano, A. et al., Enteroparasitosis infantil intestinal en Argentina. Medicina (Buenos Aires) 2000; 60: 23-4.
Olds G.R. et al., "Double-blind Placebo-controlled Study of Concurrent Administration of Albendazole and Praziquantel in Schoolchildren with Schistosomiasis and Geohelminths", J Infect Dis. 1999; 179: 996-1003.
Palomares-Alonso F. et al, "Efficacy of nitazoxanide, tizoxanide and tizoxanide/albendazole sulphoxide combination against *Taenia crassiceps* cysts" J Antimicro Chemother. 2007, 59: 212-218.
Paolini V. et al., "In vitro effects of three woody plant and sainfoin extracts on $3^{rd}$-stage larvae and adult worms of three gastrointestinal nematodes", Parasitology 2004; 129(Pt 1): 69-77.
Rabel B. et al. "Improved bioassay for estimation of inhibitory effects of ovine gastrointestinal mucus and anthelmintics on nematode larval migration"; Int'l J Parasitology 1994; 24(5): 671-676.
Rodriguez-Garcia R. et al, "[Effectiveness and safety of mebendazole compared to nitazoxanide in the treatment of Giardia lamblia in children]" Rev Gastroenterol Mex. 1999, vol. 64(3): 122-126.
Salomón, M.C. et al. Parasitol. Latinoam. V.62 n. 1-2 Santiago, Jun. 2007.
Sirivichayakul C. et al., "A comparative trial of Albendazole alone versus combination of Albendazole and Praxiquantel for treatment of *Trichuris* Trichiura Infection", Southeast Asian J Trop Med Public Health. 2001 32(2): 297-301.
Soukhathammavong P.A. et al., "Low Efficacy of Single-dose Albendazole and Mebendazole against hookworm and effect on concomitant Helminth infection in Lao PDR", PLoS Neg Trop Dis. 2012; 6(1): e1417.

(Continued)

*Primary Examiner* — Gollamudi Kishore
*Assistant Examiner* — Amanda Heyes
(74) *Attorney, Agent, or Firm* — Knobbe Martens Olson & Bear LLP

(57) ABSTRACT

Disclosed is a pharmaceutical nitazoxanide composition comprising: (a) an immediate release fraction comprising nitazoxanide non-coated granules or non-granulated powder, and (b) a pH-dependent release fraction comprising granules of nitazoxanide coated with one or more polymers having a pH-dependent solubility.

9 Claims, 2 Drawing Sheets

(56) References Cited

OTHER PUBLICATIONS

Wagland B.M. et al., "A new simplified assay for larval migration inhibition", Int'l J Parasitology 1992, 22(8): 1183-1185.
El-On, J. "Benzimidazole Treatment of Cystic Echinococcosis", Acta Tropica (2003), 85:243-252.
Fox L.M. et al., "Nitazoxanide: A New Thiazolide Antiparasitic Agent", Reviews of Anti-Invective Agents—CID (Apr. 2005), 40:1174-1180.
Pérez-Molina J. et al., "Evaluation of Nitazoxanide for the Treatment of Disseminated Cystic Echinococcosis: Report of five Cases and Literature Review", Am J Trop Med Hyg. (2011) 84(2):351-356.
Stettler M. et al., "Secondary and primary murine alveolar echinococcosis: combined albendazole/nitazoxankle chemotherapy exhibits profound anti-parasitic activity", Int J Parasit. (2004) 34:615-624.
Stockis A. et al., "Nitazoxanide pharmacokinetics and tolerability in man during 7 days dosing with 0.5 g and 1 gb.i.d.", Int J Clin Pharmacol Ther. (May 2002) 40(5):221-227.
Restriction Requirement dated Mar. 7, 2016 for U.S. Appl. No. 14/431,623, filed Mar. 26, 2015.
Response to Restriction Requirement filed May 2, 2016 for U.S. Appl. No. 14/431,623, filed Mar. 26, 2015.
Tritten L. et al., Nitazoxanide: In vitro and in vivo drug effects against *Trichuris muris* and *Ancylostoma ceylanicum* alone or in combination. Int'l J Parasit. Drugs & Drug Resist. (2012) 2: 98-105.
Dayan A.D., Albendazole, mebendazole and praziquantel. Review of non-clinical toxicity and pharmacokinetics. Acta Tropics (2003) 86: 141-159.
Non-Final Office Action dated Jun. 16, 2016 for U.S. Appl. No. 14/431,623, filed Mar. 26, 2015.
Amendment and Response dated Sep. 14, 2016 for U.S. Appl. No. 14/431,623, filed Mar. 26, 2015.
Guatemala Third Party Observations of Mar. 30, 2016 in File No. A-201400165, Siegfried Rheins. A. De C.V.; 24 pages.

\* cited by examiner

NITAZOXADINE COMPOSITION AND PROCESS TO PREPARE SAME

RELATED APPLICATIONS

This application is the U.S. National Phase of International Application No. PCT/IB2012/050380 filed Jan. 27, 2012 and published on Aug. 1, 2013 as WO 2013/110975.

FIELD OF THE INVENTION

The present invention relates to pharmaceutical compositions for oral administration of nitazoxanide in granules for suspension and the process to prepare same. The compositions of the present invention are useful for the treatment of intestinal parasitic infections and have an improved profile of gastrointestinal side effects compared to the existing formulations. The compositions of the present invention have moieties with different release profile of the active ingredient: (a) a moiety of immediate release, (b) a moiety of pH-dependent release that starts releasing between pH 5.0 and pH 7.5. Optionally, the moiety that pH-dependently releases, may comprise two moieties, a moiety that starts releasing between pH 5.0 and pH 6.0 and another moiety that starts releasing between pH 6.5 and pH 7.5. The compositions of the present invention can be delivered in a single daily dose or even allow the delivery of the whole treatment as a single dose.

BACKGROUNDS OF THE INVENTION

Nitazoxanide is a 5-nitrotiazol with antibacterial and antiparasitic activity with a broad spectrum action. Its chemical formula is 2-acetolyloxy-N-(5-nitro-2-tiazolyl) benzamide and has the following structure:

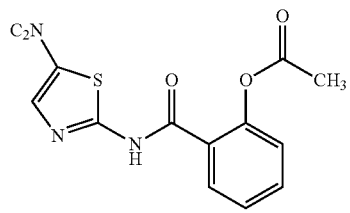

The procedure for the synthesis of nitazoxanide and the use thereof were originally disclosed by Rossignol in U.S. Pat. No. 3,950,351. U.S. Pat. No. 5,387,598 discloses nitazoxanide formulations suitable for the treatment of intestinal parasitic infections improved through the use of surfactant excipients and starch. U.S. Pat. No. 5,968,961 discloses nitazoxanide formulations with optimal particle size to achieve the therapeutic effect and reduce the side effects. U.S. Pat. No. 6,117,894 discloses improved nitazoxanide formulations in terms of stability through the use of acidifying excipients. US patent application 20100209505 discloses nitazoxanide compositions in double-coated tablets where one coating is of immediate release and the other coating is a controlled-release coating specifically designed for the treatment of chronic viral hepatitis C.

Nitazoxanide is currently approved in several countries for the treatment of infections caused by parasites in two pharmaceutical forms: immediate-release tablets and powder for immediate release suspension. These formulations require the delivery of 1 intake every 12 hours. Depending on the age of the patient the following dosage schedule and method of administration are used:

| Age | Posology | Total daily dose |
| --- | --- | --- |
| 1 to 3 Years | 100 mg every 12 hours | 200 mg |
| 4 to 11 years | 200 mg every 12 hours | 400 mg |
| 12 to 15 years | 300 mg every 12 hours | 600 mg |
| 16 years or more | 500 mg every 12 hours | 1000 mg |

The main side effects of nitazoxanide are gastrointestinal, the most frequent ones being: abdominal pain, diarrhea, nausea and vomiting. These effects increase as the dose increases. The gastrointestinal side effects of the known nitazoxanide formulations are very frequent and cause that a significant percentage of patients do not complete the treatment. Partial compliance with the treatment generates recurrence of the infection and increases the likelihood of generating resistance to the drug.

Therefore, there is a need for an improved nitazoxanide formulation for the treatment of parasitic infections that will allow a better tolerance and better compliance with the treatment.

It should be noted that the controlled-release composition in tablets disclosed by Rossignol in US patent application 20100209505 is not adequate for solving the raised problem due to several reasons. The formulation disclosed by Rossignol is specifically designed for the treatment of chronic viral hepatitis C (systemic treatment that requires high nitazoxanide plasma levels). In the aforementioned patent application, the inventor uses high viscosity polymers such as hydroxypropyl-methylcellulose (Methocel) or hydroxypropyl-cellulose (Klucel) that when they hydrate and swell remain longer in the stomach (gastro retention phenomenon). In this way they achieve the gradual release of the active ingredient in the higher absorption area of nitazoxanide (in the stomach and first portion of the gut). The controlled-release tablets disclosed by Rossignol do not achieve a sufficient reduction of the gastrointestinal side effects. As reported in the aforementioned patent application, the most common side effects for the dose of 675 mg. were: Diarrhea 33%, 25% Nausea and abdominal pain 17%.

On the other hand, the controlled-release tablets described by Rossignol containing 675 mg of nitazoxanide are very bulky, they have a weight higher than 1000 mg. This type of tablets is not suitable for pediatric or adult patients with swallowing problems due to its large size.

For these reasons, it was aimed to find a composition that would be able to overcome these drawbacks, which resulted in the present invention. In the present invention, we designed a nitazoxanide composition capable of releasing the active ingredient in pulses in order to distribute the active ingredient throughout the intestinal tract and allow for a better tolerance. We have achieved that the release of nitazoxanide focused to different regions of the digestive system would significantly reduce the side effects of the treatment. After numerous tests, it has been found that the composition of the present invention manages to obtain the desired dissolution profile by combining an immediate release moiety and at least a pH-dependent release moiety.

DETAILED DESCRIPTION OF THE INVENTION

Figure 1:
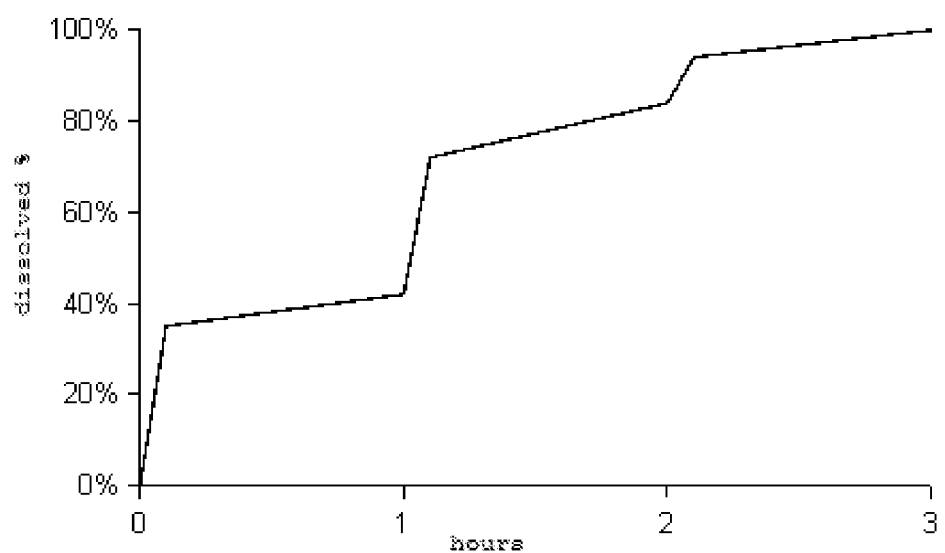
FIG. 1 shows the in-vitro dissolution profile of the suspension of Example 6.
Figure 2:
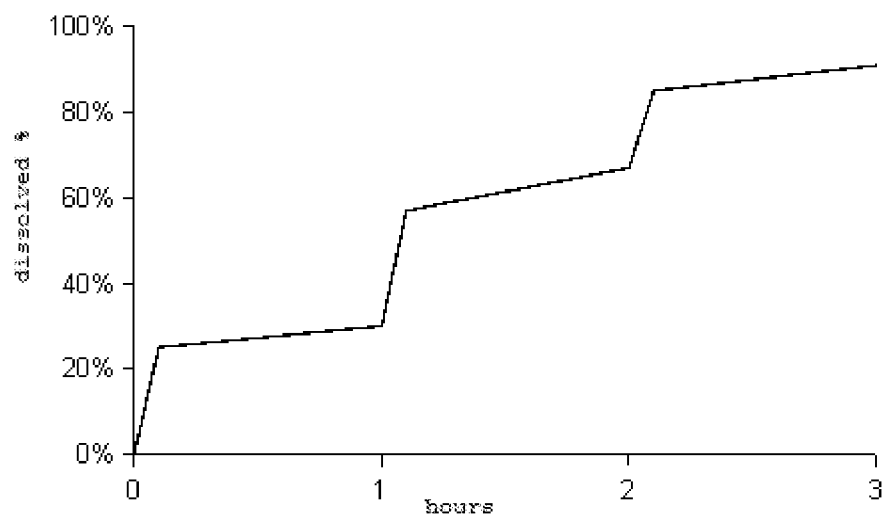
FIG. 2 shows the in-vitro dissolution profile of the suspension of Example 8.

The compositions of the present invention combine an immediate release moiety and a pH-dependent release moiety. The immediate release moiety can be made as powder or as immediate-release granules. The pH-dependent release moieties comprise coated granules with a particle-size of less than 850 microns. The pH-dependent release moiety starts releasing between pH 5.0 and pH 7.5. Optionally, the moiety that pH-dependently releases, may comprise two moieties, a moiety that starts releasing between pH 5.0 and pH 6.0 and another moiety that starts releasing between pH 6.5 and pH 7.5.

The manufacturing process comprises the following steps: 1) manufacture of pH-dependent release granules; 2) manufacture of the immediate-release moiety; 3) manufacture of the mixture of the moieties along with additional excipients for the formulation of the suspension; and 4) filling the mixture in sachets or vials.

1—Manufacture of pH-Dependent Release Granules

The overall process comprises two steps. In a first step, the granules (uncoated) are prepared and then coated with at least one pH-dependent solubility polymer as a medium to regulate the active ingredient release.

1.A—Granulation

The first step to manufacture coated granules is the manufacture of immediate-release granules. The immediate-release granules are comprised by nitazoxanide and at least one binder excipient. These granules can be manufactured using the following techniques: (1) conventional wet granulation (for example in granulation in high impact blender-granulation equipment), (2) dry granulation (compaction), (3) granulation by the extrusion-spheronization method, or (4) by the application of the active ingredient on an inert core. The preferred method is the application of the active ingredient on a inert granule as it allows to obtain spherical granules, with a smooth surface, fine sized and with a delimited particle size distribution. These features are important to ensure that when coating the granules, the sought dissolution profile is systematically obtained.

The general method of application of nitazoxanide on inert cores comprises the following steps: in an adequate capacity reactor, add purified water. Add a binding agent and keep on stirring until complete dissolution of same. Then, add the nitazoxanide and continue to stir to generate a dispersion. Optionally, disintegrating and/or stabilizing agents may be added in this step. Spray the obtained dispersion on the inert cores using a fluid bed equipped with "Wurster" insert or a tangential rotor. Dry the obtained granules.

The inert core is preferably, spherical. It may be comprised by sugar, starch, mannitol, xylitol, microcrystalline cellulose and organic acids, such as fumaric acid or tartaric acid. Preferably, the inert cores used are of microcrystalline cellulose. More preferably, the microcrystalline cellulose cores are spherical and have a size of less than 700 microns, preferably between 150 to 700 microns. Preferably, the microcrystalline cellulose Celphere CP203 cores manufactured by Asahi Kasei with a size between 150 and 300 microns, are used. The inert cores represent between 50% and 80% of the weight of the granule before coating. Preferably, the represent between 60% and 70% of the weight of the granule before coating.

The binding agent is a soluble polymer selected from hydroxypropyl-cellulose (HPC), hypromellose (HPMPC), polyvinylpyrrolidone (PVP), polyvinyl alcohol (PVA) and vinylpyrrolidone-vinyl acetate copolymer. Preferably, PVP K30 is used. The binder concentration is usually between 5% and 30% of the weight of the granule before coating. Preferably, it represents between 10% and 20% of the weight of the granule before coating.

The nitazoxanide concentration in the granule (before coating) is between 10% and 60% of the weight of the granule. Preferably, it represents between 20% and 50% of the weight of the granule before coating.

In case of adding a stabilizing agent, same is an acidifier selected between citric acid, glutamic acid, succinic acid, tartaric acid, adipic acid, malic acid, fumaric acid, ascorbic acid and mixtures thereof. The preferred stabilizing agent is citric acid, in a preferred concentration between 0.1% and 1% of the weight of the granule before coating.

In case of adding a disintegrating agent, it is preferred that same is sodium croscarmellose, sodium glycolate starch or crospovidone. The preferred concentration of the super-disintegrating agent is between 1% and 10% of the weight of the granule before coating.

1.B Coating

The coating process comprises the following steps:
(a) in an adequate capacity reactor, prepare a coating solution or suspension containing at least one pH-dependent solubility polymer. Optionally, add plasticizer agents, antitacking agents and regulators of pH.
(c) using a fluid bed equipment with Wurster insert, spray the coating solution or suspension on the granules obtained in step 1.A.
(d) once the application complete, dry the product.

The granules are coated with one or more pH-dependent solubility polymers chosen from cellulose acetate phthalate, hydroxypropylmethylcellulose phthalate, hydroxypropylmethylcellulose acetate succinate, polyvynilacetate phthalate and methacrylic acid copolymers. The methacrylic acid copolymers, alone or combined, being preferred. The adjustment of the pH from which the membrane is dissolved through the combination of different polymers is possible. It is also possible partially neutralize the acidic groups of polymers to adjust the pH from which they are dissolved. For such ends, alkalizing agents such as sodium hydroxide, sodium bicarbonate or other, are used.

For the manufacturing of granules which start releasing at a pH above 5.5, the preferred polymer is the methacrylic acid-ethyl acrylate copolymer. The polymer concentration with the coated granule ranges between 7% and 40%, and preferably, it is between 10% and 25%.

For the manufacturing of granules which start releasing at a pH above 7.0, the preferred polymer comprises the mixtures of two polymers: (1) methacrylic acid copolymer—methyl methacrylate and (2) methacrylic acid copolymer—ethyl acrylate. The polymer concentration in the coated granule ranges between 7% and 40%, and preferably, it is between 10% and 25%. The mixture of polymers can be done in equal parts or by using a greater amount of methacrylic acid-methyl methacrylate copolymer versus methacrylic acid-ethyl acrylate, the preferred ration being 75:25.

Examples of plasticizer agents include: triacetin, tributylcitrate, triethylcitrate, diethylphtalate, castor oil, dibutylsebacate, acetylated monoglycerides, medium chain triglycerides, and similar compounds, the use of medium-chain triglycerides being preferred. The plasticizer agent usually represents between 10% and 20 weight % of the coating polymers.

Examples of antitacking agents include: talc, glyceryl monostearate and agents formulated as the Plasacryl T20.

2—Manufacture of the Immediate Release Moiety

The nitazoxanide immediate release moiety may be comprised by the uncoated granules described in step 1.A, or it may be a non-granulated powder.

3—Manufacture of the Mixture of the Moieties and Formulation of the Suspension

Once the weight of each of the moieties (immediate release and pH-dependent release) aimed to be dosed is defined, perform a simple mixture of said moieties along with the additional excipients used to formulate the suspension. The additional excipients may include: sweeteners, thickeners, pH regulators, preservatives, dyes and flavoring essences. To avoid the segregation of the mixture, it is preferred that the different moieties and the additional excipients used have a similar particle size.

When mixing the moieties, the immediate release moiety contains between 20% and 50% of the total dose. The pH-dependent release moiety contains between 50% and 80% of the total dose.

4—Mixture Dosage

Once the mixture of the 3 moieties along with the excipients used to formulate the suspension is obtained, the mixture is filled into sachets or vials with the following active ingredient contents:

4.A Dosage for Treatment with One Dose Per Day for 3 Days

| Nitazoxanide over monodose amount | Number of sachets per package | Nitazoxanide amount per treatment | Age of the patient |
| --- | --- | --- | --- |
| 200 mg | 3 | 600 mg | 1 to 3 Years |
| 400 mg | 3 | 1200 mg | 4 to 11 years |
| 600 mg | 3 | 1800 mg | 12 to 15 years |
| 1000 mg | 3 | 3000 mg | 16 years or more |

4.B Dosage for Treatment with a Single Dose

| Nitazoxanide amount per vial | Number of vials | Nitazoxanide amount per treatment | Age of the patient |
| --- | --- | --- | --- |
| 600 mg | 1 | 600 mg | 1 to 3 Years |
| 1200 mg | 1 | 1200 mg | 4 to 11 years |
| 1800 mg | 1 | 1800 mg | 12 to 15 years |
| 3000 mg | 1 | 3000 mg | 16 years or more |

Measurement of the In-Vitro Dissolution Profile:

The dissolution profile of the composition is measured using the following procedure:

Device: 2 USP (Palettes)
Speed: 100 RPM
Volume: 1000 ml
Temperature: 25° C. or 37° C. (at 25° C. there is a reduced degradation of the active ingredient)
Dissolution Medium:
Step 1: 60 Minutes in 0.1N hydrochloric acid with 6% of cetyltrimethylammonium bromide
Step 2: 60 Minutes in phosphate buffer pH 5.5 with 6% of cetyltrimethylammonium bromide
Step 3: 60 Minutes in phosphate buffer pH 7.0 with 6% of cetyltrimethylammonium bromide The immediate release moiety releases as follows:

| Time | Step | Specification |
| --- | --- | --- |
| 1 h | Step 1 (acid pH) | >80% |

The pH-dependent release moiety that releases at pH 5.5 or higher, releases as follows:

| Time | Step | Specification |
| --- | --- | --- |
| 1 h | Step 1 (acid pH) | <10% |
| 2 h | Step 2 (pH 5.5) | >80% |

The pH-dependent release moiety that releases at pH 7.0 or higher, releases as follows:

| Time | Step | Specification |
| --- | --- | --- |
| 1 h | Step 1 (acid pH) | <10% |
| 2 h | Step 2 (pH 5.5) | <10% |
| 3 h | Step 3 (pH 7.0) | >80% |

The suspensions of the present invention comprising the three moieties, release the active ingredient as follows:

| Time | Step | Specification |
| --- | --- | --- |
| 1 h | Step 1 (acid pH) | 25%-55% |
| 2 h | Step 2 (pH 5.5 ) | 55%-85% |
| 3 h | Step 3 (pH 7.0 ) | >85% |

EXAMPLES OF IMPLEMENTATION

Example 1

Manufacture a 3 kg Batch of Immediate Release Granules.

For the manufacture of a 3 kg batch of immediate-release granules, the following materials were used.

| Material | Function | Amount per batch (grams) |
| --- | --- | --- |
| Nitazoxanide <100 μ (Romark Labs.) | Active Ingredient | 690.00 |
| Microcrystalline cellulose in spheres, USP/NF (Celphere CP203, Asahi Kasei) | Inert Core | 1906.80 |
| Polyvinylpyrrolidone K30, USP/NF (Plasdone K29/32, ISP Corp. ) | Binder | 402.50 |
| Anhydrous citric acid, USP/NF (Jungbunzlauer AG) | Stabilizer | 0.70 |
| Purified Water | Carrier | 5750.00 ml |
| | (evaporates during the process) | |
| Total | | 3000.00 |

Manufacturing Process: 1—Preparation by dispersion: In an adequate capacity reactor, add the established amount of purified water. Then, add the binding agent (Polyvynylpyrrolydine K30) and keep on stirring until the complete dissolution of same. Once dissolved, add the stabilizing agent (anhydrous citric acid) verifying its complete dissolution. Finally, add the Nitazoxanide and keep on stirring until an homogeneous dispersion is obtained. 2—Integrate the microcrystalline cellulose spheres in a fluid bed equipped with "wurster" insert or tangential rotor and spray the dispersion as obtained in step 1. 3—After the application is complete, dry the obtained granules.

Example 2

Manufacture of a pH-Dependent Release Granules Batch Coated with a Film Soluble at a pH Above 5.5.

For the manufacture of the batch, the following materials were used:

| Material | Function | Amount per batch (grams) |
|---|---|---|
| Immediate release granules (of Example 1) | — | 1000.00 |
| Methacrylic acid copolymer-ethyl acrylate, USP/NF (Eudragit L100-55, Evonik) | Release regulator polymer | 140.00 |
| Sodium hydroxide, USP/NF (Merck) | Release pH modulator | 1.90 |
| Triethylcitrate, USP/NF (Vertellus Performance Materials) | Plasticizer Agent | 14.00 |
| Talc, USP/NF (Magnesita Refractarios) | Antitacking agent | 56.00 |
| Purified Water | Carrier (evaporates during the process) | 1120.00 ml |
| Total | | 1211.90 |

Manufacturing Process: 1) In an adequate capacity reactor, add the established amount of purified water. Then add the release regulator polymer (Eudragit L100-55) and keep on stirring until an homogeneous dispersion is obtained. Add the sodium hydroxide and then the plasticizer agent (Triethylcitrate). Finally, incorporate the talc while maintaining the stirring until an homogeneous dispersion is obtained.
2—Integrate the immediate release granules of nitazoxanide in a fluid bed equipped with "wurster" insert or tangential rotor and then spray the dispersion as obtained in step 1.
3—After the application is complete, dry the obtained granules.

Percentage Composition of Granules that Start Releasing at pH 5.5

| | |
|---|---|
| Nitazoxanide <100 μ (Romark Labs.) | 18.98% |
| Microcrystalline cellulose in spheres, USP/NF (Celphere CP203, Asahi Kasei) | 52.45% |
| Polyvinylpyrrolidone K30, USP/NF (Plasdone K29/32, ISP Corp. ) | 11.07% |
| Anhydrous citric acid, USP/NF (Jungbunzlauer AG) | 0.02% |
| Methacrylic acid copolymer-ethyl acrylate, USP/NF (Eudragit L100-55, Evonik) | 11.55% |
| Sodium hydroxide, USP/NF (Merck) | 0.16% |
| Triethylcitrate, USP/NF (Vertellus Performance Materials) | 1.15% |
| Talc, USP/NF (Magnesita Refractarios) | 4.62% |
| Total | 100.00% |

Example 3

Manufacture of a ph-Dependent Release Granules Batch Coated with a Film Soluble at a ph Above 7.0.

For the manufacture of the batch, the following materials were used:

| Material | Function | Amount per batch (grams) |
|---|---|---|
| Immediate release granules (of Example 1) | — | 1000.00 |
| Methacrylic acid copolymer-methyl methacrylate (1:2), USP/NF (Eudragit S100, Evonik) | Release regulator polymer | 105.00 |
| Methacrylic acid copolymer-ethyl acrylate, USP/NF (Eudragit L100-55, Evonik) | Release regulator polymer | 35.00 |
| Medium-chain triglycerides, NF (Miglyol 812, Sasol) | Plasticizer Agent | 14.00 |
| Talc, USP/NF (Magnesita Refractarios) | Antitacking agent | 14.00 |
| Magnesium Stearate, USP/NF (Mallinckrodt) | Antitacking agent | 14,00 |
| Ethyl Alcohol (Fradealco) | Carrier (evaporates during the process) | 1866.66 ml |
| Total | | 1182.00 |

Manufacturing Process: 1) Manufacture of the coating solutions to be used: Integrate the Eudragit L100-55 and Eudragit S100 in a reactor with the established amount of ethanol and keep on stirring until the complete dissolution of the polymers is observed. Then integrate the plasticizer agent (medium-chain triglycerides) and finally add the magnesium stearate until an a homogeneous dispersion is obtained. 2—Integrate the immediate release granules of nitazoxanide in a fluid bed equipped with "wurster" insert or tangential rotor and then spray the polymer-containing dispersion over the granules. Add talc in a staggered manner during the process so as to reduce the tacking. 3) After the application is complete, dry the obtained granules.

Percentage Composition of Granules that Start Releasing at pH 7.0

| | |
|---|---|
| Nitazoxanide <100 µ (Romark Labs.) | 19.46% |
| Microcrystalline cellulose in spheres, USP/NF (Celphere CP203, Asahi Kasei) | 53.77% |
| Polyvinylpyrrolidone K30, USP/NF (Plasdone K29/32, ISP Corp.) | 11.35% |
| Anhydrous citric acid, USP/NF (Jungbunzlauer AG) | 0.02% |
| Methacrylic acid copolymer-methyl methacrylate (1:2), USP/NF (Eudragit S100, Evonik) | 8.87% |
| Methacrylic acid copolymer-ethyl acrylate, USP/NF (Eudragit L100-55, Evonik) | 2.96% |
| Medium-chain triglycerides, NF (Miglyol 812, Sasol) | 1.19% |
| Talc, USP/NF (Magnesita Refractarios) | 1.19% |
| Magnesium Stearate, USP/NF (Mallinckrodt) | 1.19% |
| Total | 100.00% |

Example 4

Manufacture of Immediate Release Powder

For the manufacture of a 21 kg batch of the immediate release moiety, the following materials were used.

| | g | % |
|---|---|---|
| Nitazoxanide <100 µ (Romark Labs.) | 250.00 | 1.19% |
| Refined Sugar, USP/NF (Ledesma) | 20000.00 | 95.24% |
| Microcrystalline cellulose and sodium carboxymethylcellulose, USP/NF (Avicel RC-591, FMC) | 628.00 | 2.99% |
| Yellow Dye (Vidhi Dyestuffs) | 2.00 | 0.01% |
| Strawberry powder essence (RBP 100043, Saporiti) | 120.00 | 0.57% |
| Total | 21000.00 | 100.00% |

Manufacturing Process: In an adequate mixer, mix Avicel RC-591, yellow dye, strawberry powder essence and half of the sugar. Then, integrate the nitazoxanide and mix again. Finally, add the remaining half of the sugar and mix until an homogeneous mixture is obtained.

Example 5

Manufacture of the Mixture for Suspension Containing 2 Pulses. 40% Immediate Release and 60% Release at pH 5.5

In a double cone mixer the following materials were mixed for 15 minutes: 70 grams of the granules of Example 2 (pH 5.5) and 750 g of the immediate release powder of Example 4.

| Component | Amount (g) | Nitazoxanide content (g) | Amount of the active ingredient content in each moiety. |
|---|---|---|---|
| Granules of Example 2 (pH 5.5) | 70 | 13.29 | 59.8% |
| Immediate release powder of Example 4 | 750 | 8.92 | 40.2% |
| Total mixture | 820 | 22.21 | 100% |

Analytical Results:
Nitazoxanide content in the mixture: 20 mg/g.
Dissolution test using 30 g of the product (equivalent to 600 mg of nitazoxanide) per flask:

| Time | Step | Specification | Results |
|---|---|---|---|
| 1 h | Step 1 (acid pH) | 25%-55% | 39% |
| 2 h | Step 2 (pH 5.5) | >85% | 94% |

Conclusion: The product complies with the desired profile.

Example 6

Manufacture of the Mixture for Suspension Containing 3 Pulses. 35% Immediate Release, 45% Release at pH 7.0 and 20% Release at pH 7.0.

In a double cone mixer the following materials were mixed for 15 minutes: 968 grams of the granules of Example 2 (pH 5.5), 420 g of the granules of Example 3 (pH 7.0) and 12000 g of the immediate release powder of Example 4.

| Component | Amount (g) | Nitazoxanide content (g) | Amount of the active ingredient content in each moiety. |
|---|---|---|---|
| Granules of Example 2 (pH 5.5) | 968 | 183.73 | 45% |
| Granules of Example 3 (pH 7.0) | 420 | 81.73 | 20% |
| Immediate release powder of Example 4 | 12000 | 142.80 | 35% |
| Total mixture | 13388 | 408.26 | 100% |

Analytical Results:
Nitazoxanide content in the mixture: 31 mg/g
Dissolution test using 32.25 g of the product (equivalent to 1 g of nitazoxanide) per flask:

| Time | Step | Specification | Results |
|---|---|---|---|
| 1 h | Step 1 (acid pH) | 25%-55% | 42% |
| 2 h | Step 2 (pH 5.5) | 55%-85% | 84% |
| 3 h | Step 3 (pH 7.0) | >85% | 95% |

Conclusion: The product complies with the desired profile.

Example 7

Furnishing in Sachets 300 sachets, each containing 32.25 g of mixture for suspension (equivalent to 1 g of nitazoxanide) were filled.

The formula of each sachet is the following:

| | Contents per sachet (g) |
|---|---|
| Nitazoxanide <100 µ (Romark Labs.) | 1,00 |
| Refined Sugar, USP/NF (Ledesma) | 27,52 |
| Microcrystalline cellulose in spheres, USP/NF (Celphere CP203, Asahi Kasei) | 1,77 |
| Microcrystalline cellulose and sodium carboxymethylcellulose, USP/NF (Avicel RC-591, FMC) | 0,86 |
| Polyvinylpyrrolidone K30, USP/NF (Plasdone K29/32, ISP Corp.) | 0,37 |
| Methacrylic acid copolymer-ethyl acrylate, USP/NF (Eudragit L100-55, Evonik) | 0,30 |
| Strawberry powder essence (RBP 100043, Saporiti) | 0,16 |
| Talc, USP/NF (Magnesita Refractarios) | 0,12 |
| Methacrylic acid copolymer-methyl methacrylate (1:2), USP/NF (Eudragit S100, Evonik) | 0,09 |
| Triethylcitrate, USP/NF (Vertellus Performance Materials) | 0,03 |
| Magnesium Stearate, USP/NF (Mallinckrodt) | 0,01 |
| Medium-chain triglycerides, NF (Miglyol 812, Sasol) | 0,01 |
| Yellow Dye (Vidhi Dyestuffs) | 0,005 |
| Sodium hydroxide, USP/NF (Merck) | 0,004 |
| Anhydrous citric acid, USP/NF (Jungbunzlauer AG) | 0,001 |
| Total | 32,25 |

Example 8

Manufacture of the Mixture for Suspension Containing 3 Pulses. 29% Immediate Release, 35% Release at pH 5.5 and 36% Release at pH 7.0.

In a double cone mixer the following materials were mixed for 15 minutes: 230 grams of the granules of Example 2 (pH 5.5), 230 g of the granules of Example 3 (pH 7.0) and 3000 g of the immediate release powder of Example 4.

| Component | Amount (g) | Nitazoxanide content (g) | Amount of the active ingredient content in each moiety. |
|---|---|---|---|
| Granules of Example 2 (pH 5.5) | 230 | 43.65 | 35.2% |
| Granules of Example 3 (pH 7.0) | 230 | 44.76 | 36.0% |
| Immediate release powder of Example 4 | 3000 | 35.70 | 28.8% |
| Total mixture | 3460 | 124.11 | 100% |

Analytical Results:
Nitazoxanide content in the mixture: 36 mg/g.
Dissolution test using 83.33 g of the product (equivalent to 1 g of nitazoxanide) per flask:

| Time | Step | Specification | Results |
|---|---|---|---|
| 1 h | Step 1 (acid pH) | 25%-55% | 30% |
| 2 h | Step 2 (pH 5.5) | 55%-85% | 67% |
| 3 h | Step 3 (pH 7.0) | >85% | 91% |

Conclusion: The product complies with the desired profile.
Furnishing in Vials
40 vials, each containing 83.33 g of mixture for suspension (equivalent to 3 g of nitazoxanide) were filled.

Example 9

In order to evaluate the tolerance of the composition, a cross-linked Phase I clinical assay was performed in 24 healthy adult volunteers. As Reference formulation, the volunteers received nitazoxanide reconstituted suspension (2 g/100 ml). The dose delivered after a high calorie breakfast was of 25 ml of reconstituted suspension containing 500 mg of nitazoxanide and along with the dinner, another 25 ml of reconstituted suspension containing 500 mg of nitazoxanide. In total, 1000 mg of nitazoxanide were delivered in 2 doses of 500 mg each, with an 12 hours interval between them. As Test formulation, volunteers received the formulation of Example 7. The delivered dose was the content of 1 sachet (32.25 grams of granules for suspension, containing 1000 mg of nitazoxanide) dispersed in 150 ml of water, after a high-calorie breakfast. Inpatient and Monitoring: In the two periods of the study, the volunteers remained hospitalized during the 24 hours following administration. The period of pharmacological rest (washout) between sessions was of 7 days. After the delivery of the formulations, the Side Events were registered and a control was carried out at 48 h to verify the remission of same. Results: The following table summarizes the observed side effects (all of mild intensity), for each formulation:

| | Nitazoxadiene Reconstituted Suspension (2 g %) (500 mg BID) n = 24 | Example 7 1000 mg (QD) n = 24 |
|---|---|---|
| Abdominal Pain | 3/24 (12.5%) | 1/24 (4.2%) |
| Diarrhea | 1/24 (4.2%) | 0/24 (0%) |
| Headache | 1/24 (4.2%) | 0/24 (0%) |
| Nausea | 1/24 (4.2%) | 0/24 (0%) |
| Total events reported | 6 | 1 |

Conclusion: The study showed a greater tolerance for the Test formulation.

The invention claimed is:
1. A nitazoxanide pharmaceutical composition for oral delivery for the treatment of intestinal parasitic infections in the form of a suspension comprising:
(a) an immediate release moiety comprising nitazoxanide non-coated granules or non-granulated powder; and

(b) a pH-dependent release moiety comprising nitazoxanide-containing granules coated by one or more polymers with pH-dependent solubility;
wherein the granules of the pH-dependent release moiety start releasing nitazoxanide at a pH above 5.0.

2. A pharmaceutical composition according to claim 1, wherein the pH-dependent release moiety comprises two moieties, a first moiety comprising coated granules that starts releasing at a pH above 5.0 and a second moiety comprising coated granules that starts releasing at a pH above 6.5.

3. A pharmaceutical composition according to claim 1, wherein the pH-dependent release moiety comprises two moieties, a first moiety comprising coated granules that starts releasing at a pH above 5.5 and a second moiety comprising coated granules that starts releasing above a pH 7.0.

4. A pharmaceutical composition according to claim 1, wherein the granules of the pH-dependent release moiety are coated with one or more pH-dependent solubility polymers selected from the group consisting of cellulose acetate phthalate, hydroxypropylmethylcellulose phthalate, hydroxypropylmethylcellulose acetate succinate, polyvinylacetate phthalate and methacrylic acid copolymers.

5. A pharmaceutical composition according to claim 1, wherein the granules of the pH-dependent release moiety are coated with methacrylic acid copolymers.

6. A pharmaceutical composition according to claim 3, wherein the granules that start releasing at a pH above 5.5 are coated with methacrylic acid copolymer-ethyl acrylate, the methacrylic acid copolymer-ethyl acrylate has a plurality of acid groups which have been contacted with sodium hydroxide, and the granules that start releasing at a pH above 7.0 are coated with a mixture of methacrylic acid-methyl methacrylate copolymer and methacrylic acid-ethyl acrylate copolymer.

7. A pharmaceutical composition according to claim 1, wherein the coated granules of the pH-dependent release moiety have a particle size of less than 850 microns.

8. Monodose sachets comprising a pharmaceutical composition according to claim 1, wherein each sachet includes from 200 to 1000 mg of nitazoxanide.

9. Vials comprising a pharmaceutical composition according to claim 1, wherein each vial includes from 600 to 3000 mg of nitazoxanide.

* * * * *